(12) United States Patent
Dylla (10) Patent No.: US 11,328,348 B2
(45) Date of Patent: May 10, 2022

(54) OBFUSCATED SERVICE PROVIDER IDENTITY DURING CLIENT SELECTION

(71) Applicant: Truoth, LLC, Shorewood, MN (US)

(72) Inventor: Russell A. Dylla, Shorewood, MN (US)

(*) Notice: Subject to any disclaimer, the term of this patent is extended or adjusted under 35 U.S.C. 154(b) by 527 days.

(21) Appl. No.: 16/539,702

(22) Filed: Aug. 13, 2019

(65) Prior Publication Data

US 2020/0051161 A1 Feb. 13, 2020

Related U.S. Application Data

(60) Provisional application No. 62/718,315, filed on Aug. 13, 2018.

(51) Int. Cl.
| | | |
|---|---|---|
| *G06Q 30/08* | (2012.01) | |
| *G06Q 30/06* | (2012.01) | |
| *G16H 40/20* | (2018.01) | |
| *G06F 21/62* | (2013.01) | |

(52) U.S. Cl.
CPC ......... *G06Q 30/08* (2013.01); *G06F 21/6254* (2013.01); *G06Q 30/0615* (2013.01); *G06Q 30/0619* (2013.01); *G16H 40/20* (2018.01); *G06Q 30/0613* (2013.01); *G06Q 30/0617* (2013.01)

(58) Field of Classification Search
None
See application file for complete search history.

(56) References Cited

U.S. PATENT DOCUMENTS

| | | | |
|---|---|---|---|
| 8,688,594 B2* | 4/2014 | Thomas | G06Q 30/06 705/314 |
| 10,600,096 B2* | 3/2020 | McQuade | G06Q 30/08 |
| 10,963,848 B1* | 3/2021 | Anderson | G06Q 20/08 |
| 2004/0133451 A1* | 7/2004 | Kleinschmidt | G16H 10/60 705/26.1 |
| 2006/0161468 A1* | 7/2006 | Larsen | G06Q 10/1095 705/80 |

(Continued)

OTHER PUBLICATIONS

Masaud-Wahaishi, A., et al., "Agent-Oriented Privacy-Based Information Brokering Architecture for Healthcare Environments," International Journal of Telemedicine and Applications, 2009, Hindawi Limited. (Year: 2009).*

(Continued)

*Primary Examiner* — Nicholas D Rosen
(74) *Attorney, Agent, or Firm* — Carlson, Caspers, Vandenburgh & Lindquist, P.A.

(57) ABSTRACT

A method for matching a client with a service provider is provided. The method includes receiving a request for a service from a client device, selecting one or more service providers based on the location indicated for the service, comparing the request to one or more profiles for the one or more service providers and to available services times, generating at least one bid for the service based on the one or more profiles, and sending the at least one bid to the client device. Sending the at least one bid includes obfuscating, to the client device, the identity of the one or more service providers corresponding to the at least one bid. The method also includes receiving from the client device a selection of one of the at least one bids and sending to the client device the specific identity of the one or more service providers.

14 Claims, 9 Drawing Sheets

(56) References Cited

U.S. PATENT DOCUMENTS

| | | | |
|---|---|---|---|
| 2006/0224490 A1* | 10/2006 | Seth | G06Q 10/1097 705/37 |
| 2008/0046336 A1* | 2/2008 | Mosleh | G06Q 30/02 705/26.62 |
| 2012/0136527 A1* | 5/2012 | McQuade | G06Q 30/08 705/26.4 |
| 2012/0246024 A1* | 9/2012 | Thomas | G06Q 30/06 705/27.1 |

OTHER PUBLICATIONS

Anon., "Faith Based Program to Save Big On Medical Care with MediBid," PRWeb Newswire, Jan. 26, 2011. (Year: 2011).* hotwire.com, Accessed from the Internet: http://hotwire.com on Aug. 13, 2019, pp. 1-4.

medibid.com, Accessed from the Internet: http://medibid.com on Aug. 13, 2019, pp. 1-25.

* cited by examiner

OBFUSCATED SERVICE PROVIDER IDENTITY DURING CLIENT SELECTION

RELATED APPLICATIONS

This application claims the benefit of U.S. Provisional Application No. 62/718,315, entitled "AUTOMATIC BIDDING FOR CLIENT SERVICES WITH SCHEDULE INTEGRATION", which is hereby incorporated herein by reference.

BACKGROUND

Service industries desire to maximize revenue by filling available service time slots with clients. Examples of such service industries include the dental and medical fields, in which service providers maintain offices and have available time slots for dental and medical services to be performed. Service industries, however, have little way of identifying leads for prospective clients unless the client contacts them directly.

Clients of service industries desire to obtain competitive prices for their services at a time and location that is convenient. In order to obtain information on a potential service, a client usually must manually identify available service offices for that service and manually contact (e.g., call, email) a person at each desired service office to obtain available times and possibly an estimated price for the service. Because of the inconvenience of doing this for multiple different offices, clients typically contact only one or maybe two service offices to obtain information.

BRIEF DESCRIPTION

Embodiments for a method for matching a client with a service provider are provided. The method includes receiving a request for a service from a client device, the request including an indication of the service to be performed, an indication of one or more times to perform the service, and an indication of a location for the service. One or more service providers are selected based on the location indicated for the service and the request is compared to one or more profiles for the one or more service providers and to available services times for the one or more service providers. At least one bid is generated for the service based on the one or more profiles. Generating at least one bid includes identifying a profile that indicates a price for the service indicated in the request and has at least one available service time that corresponds to a length of time for the service and matches the one or more times indicated in the request. The at least one bid is sent to the client device, wherein the at least one bid is sent in a manner that obfuscates, to the client device, the identity of the one or more service providers corresponding to the at least one bid. A selection of one of the at least one bids is received from the client device and the specific identity of the one or more service providers is sent to the client device in response to the selection of a bid.

Embodiments for another method for matching a client with a service provider are also provided. The method includes receiving a request for a service from a client device, the request including an indication of the service to be performed and an indication of a location for the service, selecting one or more service providers based on the location indicated for the service, and comparing the request to one or more profiles for the one or more service providers and to available services times for the one or more service providers. A list of available service times is generated for the request. The list of available service times is sent to the client device. The list of available service times is sent in a manner that includes obfuscating, to the client device, the identity of the one or more service providers corresponding each of the available service times in the list. A selection of one of the available service times in the list of available service time is received from the client device and the specific identity of the one or more service providers is sent in response to the selection of a service time.

DRAWINGS

Understanding that the drawings depict only exemplary embodiments and are not therefore to be considered limiting in scope, the exemplary embodiments will be described with additional specificity and detail through the use of the accompanying drawings, in which.

DETAILED DESCRIPTION

Figure 1:
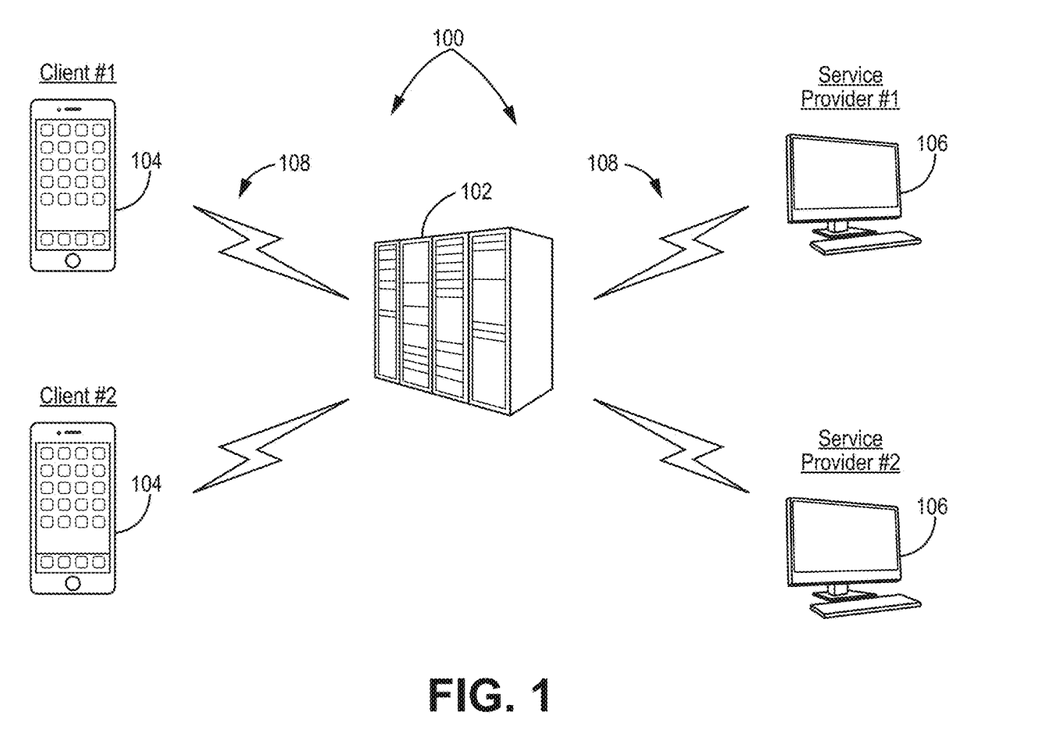
FIG. 1 is a block diagram of an example system for matching a client with a service provider.

FIG. 1 is a block diagram of an example system 100 that can provide a more convenient way for clients to obtain information regarding a prospective service, while also providing service providers access to prospective clients which they can use to fill their available service time slots. System 100 includes a backend server (e.g., web server) 102, one or more client devices 104, and one or more service provider devices 106. The backend server 102 can be communicatively coupled to the one or more client devices 104 and the one or more service provider devices 106 over one or more networks 108, including, but not limited to, a local area network, intranet, and/or the internet. Communication between the backend server 102, the client device(s) 104, and/or the provider device(s) 106 can use any appropriate protocol including Internet Protocol (IP), Hypertext Transfer Protocol (HTTP), Hypertext Transfer Protocol Secure (HTTPS), and other internet-based protocols.

The client device(s) 104 interact with a respective client, and the provider device(s) 106 interact with individuals (e.g., employees) at a respective service provider. A client is an individual desiring to have a service performed and a service provider is an entity (e.g., individual, group of individuals, business) desiring to provide services to a client.

Example service providers include a dentist (e.g., general dentist, orthodontist, prosthodontist), a medical doctor (e.g., family practice, surgeon, dermatologist, obstetrician, ophthalmologist, podiatrist, psychiatrist, sleep specialist, urologist, etc.), an optometrist, and other service providers. Example clients include an individual desiring to obtain a service provided by the service provider, such as a dental, medical, or optometrist service. Example client devices 104 and service provider devices 106 include a mobile phone, tablet, laptop, desktop computer, or wearable device. The client device(s) 104 and service provider device(s) 106 can execute respective apps, local applications, or access a webpage that enables communication with the backend server 102.

System 100 enables a client to view and select a service and timeslot for their desired service. The system 100 can make it easy for a client by automatically identifying one or more suitable service providers for the requested service. Similarly, the system 100 provides benefits to providers by presenting them with potential clients and can generate automatic bids for the requested services.

Figure 2:
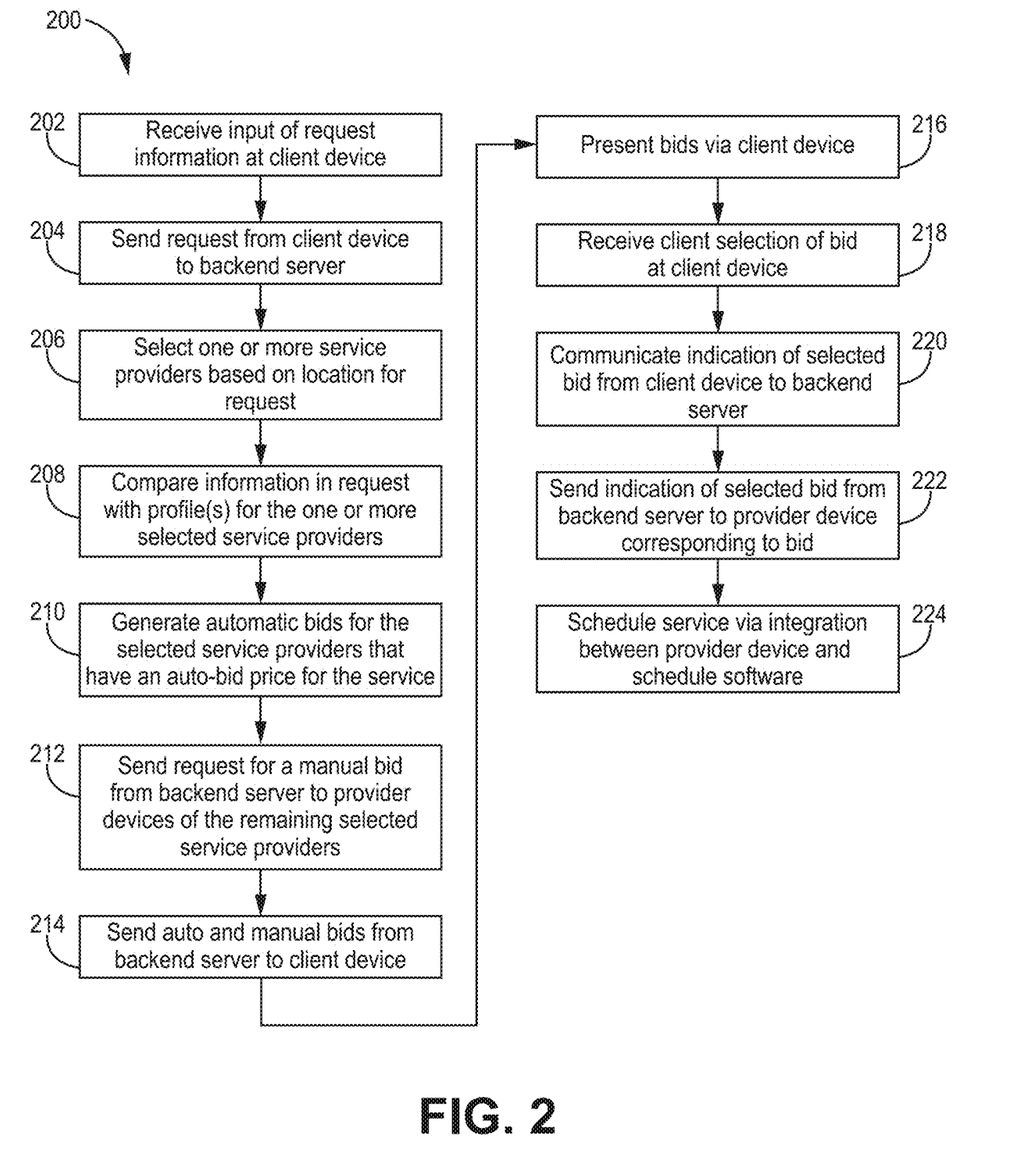
FIG. 2 is a flow diagram of an example method for matching a client with a service provider.

FIG. 2 is a flow diagram of an example method 200 for matching a client with a service provider using the system 100. Client device 104 can receive information input by a client regarding a service the client would like performed by a service provider (block 202). The client device 104 can execute software (e.g., an app, application, or webpage) that is associated with the backend server 102 to obtain the information on the request. The information can be obtained/input to the client device 104 in any suitable manner (e.g., via touch screen, keyboard, mouse, voice command, optical coding, etc.). The information obtained by the client device 104 for the request can include any suitable information, such as an indication of the service to be performed, an indication of one or more times to perform the service, and an indication of a location for the service. The indication of the service to be performed can be any suitable indication, such as a selection of one or more service options presented by the client device 104 to the client, input of a standardized code (e.g., ADA, CDT, HCUP, or ICD code) or an optical code (e.g., QR code) read by the client device that indicates the service. Such an optical code can be located on a paper received by the client, for example, from a service provider that prints such optical codes for the client on a proposed treatment plan. The location for the requested service can take any suitable form, such as a specific office location, a zip code, a city, state, or geographical region, within a radius of the client device's current location, or within a radius of an input location.

In response to obtaining information on the request from the client, the software of the client device 104 can send a request based on the information to the backend server 102 (block 204). The request can include indications of the information received from the client. For example, the request can include an indication of the service to be performed, an indication of one or more times to perform the service, and an indication of a location for the service.

In response to receiving the request, the backend server 102 can select one or more potential service providers for the request (block 206). The one or more potential service providers can be selected, at least in part, based on the location for the service. For example, the one or more service providers can be service providers within a certain distance (e.g., 15 miles) of the location in the request. Other factors can also be used to select the one or more potential service providers such as a category of service that the service provider offers (e.g., dental, medical, optical). The other factors can also include specific services offered by the service provider, such as dental cleaning, tooth extraction, etc.

The backend server 102 can then compare the information in the request with a profile for each of the one or more potential service providers selected (block 208). The backend server 102 can maintain a plurality of service provider profiles. Each profile corresponds to a service provider, and each profile can include a fee schedule associating services provided by the corresponding service provider to an auto-bid price for that service. The profile can also include other information, such as a length of time for a service, a location or room for a service, an individual or individuals for a service, equipment for a service.

The backend server 102 can also maintain a schedule of available times for each service provider. In an example, the available times can be manually provided from the respective service providers to the backend server 102. One example process of manual entry includes the available times being provided from an individual at the service provide to an individual at an entity associated with the backend server 102. The entity associated with the backend server 102 can then manually enter the available times. Another example manual entry process includes the backend server 102 providing a portal for the service providers to login to and manually input their available times directly to the backend server 102.

In another example, the available times can be automatically retrieved by the backend server 102 from software operating a provider device 106 for the provider. Software executing on the provider device 106 can integrate with scheduling software for the service provider to automatically pull available service times via an API of the scheduling software and send the available service times to the backend server 102. Instead of, or in addition to, automatically pulling available service times, software executing on the provider device 106 can receive manually input service times and send the service times to the backend server 102. Additional information can also be obtained by the backend server such as whether an available service time is a general service time, what types of service can be performed during an available service time, and/or an office location or doctor corresponding to the service time.

In any case, the backend server 102 can compare the information received from the client regarding the requested service with the profiles for the selected one or more service providers and/or the available times to generate automatic bids for correspond to the requested service (210). Generating automatic bids can include identifying which of the one or more service providers has a profile that provides an auto-bid price for the service of the request and has at least one available service time that matches a time indicated in the request. In an example, the backend server 102 can, in response to receiving a request for service from a client, generate an auto-bid for each of the selected service providers for that response having a profile listing a price corresponding to the service of the response and an available service time matching a time indicated in the request. In other examples, no time for service is received with the request for service and auto-bids are generated for each of the selected service providers for that response having a profile listing a price corresponding to the service of the response. Each auto-bid generated can indicate the price and available service time(s) for the corresponding service provider. In an example, the profile for the service provider can rank time slots, such that the backend server 102 will attempt to fill higher ranked time slots before lower ranked ones. For example, time slots between 9 am and 12 pm and 1 pm and 4 pm from Monday-Friday can be ranked the highest, while timeslots between 7-9 am and 4-6 pm and 7 am to 4 pm on Friday can be ranked lower. In an example, closer (to the present time) time slots can be selected/ranked before farther out time slots. Other rankings can also be used. The one or more auto-bids can be sent from the backend server 102 to the client device 104 for presentation to the client (block 208).

In an example, the backend server 102 can also send out a request to all or a subset of the selected service providers for manual bids for the requested service (block 212). The request(s) sent by the backend server 102 can include information corresponding to the requested service such as an indication of the service requested and an indication of one or more times to perform the service. In an example, the backend server 102 can send information corresponding to the client, while obfuscating the identity of the client. For example, the backend server 102 can provide an indication of an insurance plan of the client, an indication of a financing amount approved for the client, and/or an indication of a credit rating for the client without providing the actual identity or any information that could be used to specifically identify the client. The full identity of the client can be provided to the service provider if/when the client has selected (committed to) a particular bid and/or available time provided by that service provider. In an example, the backend server 102 can send out a request for a manual bid only to the selected service providers that do not list an auto-bid price for the service. The request(s) for a manual bid can be sent to the provider device(s) 106 for the corresponding service providers, and the provider device(s) 106 can present the request to the service provider or individual thereof. The provider device(s) 106 can receive input from the service providers or individuals thereof for manual bids in response to the request and can send information on any manual bids received to the backend server 102.

The backend server 102 can then send the automatic bids, manual bids, and/or available service times to the client device 104 for presentation to the client (block 214). In some examples, one or more available service times can be identified by the backend server 102 even if those available service times do not have an automatic or manual bid corresponding thereto. For example, the backend server 102 may have received an available service time from a service provider corresponding to one or more types of service, but the service provider does not provide an automatic or manual bid price for the service. In such a situation, the backend server 102 can provide the available service time to the client device 104 without a corresponding price.

The client device 104 can present (e.g., display) the one or more auto-bids as well as any manual bids to the client (block 216). The client device 102 can then receive a selection of one of the bids from the client (block 218). The client device 102 can communicate the selected bid to the backend server 102 (block 220), which can send corresponding information to the provider device 106 corresponding to the selected bid (block 222). The information can be sent between the devices in any suitable manner, for example, via respective APIs or via an email (e.g., an automated email from the backend server 102 to an email address for the service provider 106. In this way one or more bids for a service can be obtained by a client and selected. In an example, through integration with the scheduling software of the corresponding service provider, the service provider device (block 224) can automatically schedule the service for the client according to the selected bid received from the backend server 102.

The software on the client device 104 can enable the client to filter the bids received to aid in selecting a bid. The filters can be based on price, time of service, location, rating of service provider, and/or other factors.

The software on the provider device 106 can enable the service provider to update/override a manual or auto-bid generated for that service provider. In response to receiving an update/override of a current bid, the provider device 106 can send the update/override to the backend server 102, which can in turn send the update/override to the corresponding client device 104 for presentation to the client.

The time of service can be indicated by the client device 104 to the backend server 102, by the provider device 106 to the backend server 102, or by the backend server 102 to the client device 104 in the auto-bid in any appropriate manner. For example, the time of service can be indicated as a specific time or time period or can be a length of time from the present (e.g., same day service, within 2 days, etc.).

In addition to enabling generation and selection of automatic bids, the system 100 can collect and store information regarding the service as well as reviews and ratings for the service provider. The information collected can include a record of the treatment (e.g., what was performed, where it was performed, the cost, etc.). The record of the treatment can be sent to the backend server 102 from the client device 104 or the provider device 106. The backend server 102 can store the record of treatment and associate the record with the client account for the client who received the treatment. The backend server 102 can store multiple records for the client, including records of treatments not bid or scheduled through the system 100 to build up a service history for the client. The backend server 102 can (e.g., automatically) provide this service history to a service provider in response to a selection of a bid via the client device 104. Thus, the client's service history can be provided to the service provider for consideration in performing their service. The software on the client device 104 can also provide a means to receive a rating and/or review of the service (after it is performed) from the client. The client device 104 can send the rating and/or review to the backend server 102 which can store the rating and/or review and associate it with an account for the service provider. The backend server 102 can send the review, rating, and/or a compilation of multiple reviews and/or ratings to a client device 104 to enable the client device 104 to display the review, rating, and/or compilation thereof to a client interested in obtaining the information when considering whether to select a bid from the corresponding service provider. The backend server 102 can also send the review, rating, and/or compilation information to the corresponding service provider for that service provider to see what clients have thought of their service.

As mentioned above, in an example, the software on the client device 104 can read optical codes on papers (e.g., a proposed treatment plan) provided by a service provider to input the service requested. Software on the provider device 106 can create and print the optical code on the paper for the client. Coordinated algorithms can be used by the system 100 to create and read the optical codes so that optical codes created by the provider device(s) 106 can be read by the client device(s) 104.

The system 100 can also obtain and maintain other information on the client, such as their insurance information (e.g., dental, medical), whether they are approved for financing, and/or a credit rating. This information can be provided to a service provider for them when considering whether to submit a manual bid. In some examples, items of this information can be included in the service providers profile and linked to whether or not an auto-bid is generated. For example, a profile could indicate that an auto-bid is generated only if the client holds one of a list of insurance policies and/or an auto-bid is generated only if the client has a credit rating above a threshold. These and/or other factors can be used to give service providers control to limit which clients have automatic bids generated for them. In an example, the backend server 102 can generate a metric or set of metrics to rate the client or aspects of the client for the service provider. Example metrics can include timeliness of showing up for appointments, timeliness of payments, compliance, etc. Metric thresholds can be listed on a service providers profile causing the backend server 102 to only generate an auto-bid for a client having a metric above the threshold.

In an example, the backend server 102 can maintain data on service providers and/or clients to track service outcomes or other items. For example, the backend server 102 can track what was performed, when the service was performed, the cost, and how effective the service was. In an example, the effectiveness of the service can be determined by comparing a length of time between repeat services—that is, a length of time until the same service is repeated. In the example of dental treatment, the length of time between when a crown is installed on a given tooth and when that crown is replaced can be tracked. This information can be provided directly to a client device 104 for presentation to a client, the service provider device 106, or can be provided directly to a third party, such as an insurance company. In an example, the backend server 102 can generate one or a set of metrics for a service provider that factors in this information maintained on the service outcomes. For example, the service provider can provide an overall metric number from 0 to 10. In an example, a set of metrics such as a price metric, a service effectiveness metric, a customer rating metric, and/or other metrics can be generated.

Advantageously, the auto-bidding process described herein provides an automatic means for clients to obtain bids from one or more service providers, wherein the bids take into account the schedule in which the service can be performed. The auto-bidding process provides increased access to pricing and other information (e.g., reviews, ratings, metrics) for clients to service providers and provides more access for service providers to clients. Also, service providers can obtain information on potential clients ahead of time by reviewing client information provided by the backend server 102. Moreover, service providers are given access to a new pool of clients without much access.

An implementer of the system 100 can charge an access fee to the service providers and/or clients to set up an account and/or download the software for the client device 104 or provider device 106 respectively. The access fee can have any appropriate form such as a one-time fee, a monthly subscription, or a per request/bid fee. In an example, the implementer of the system 100 can sell add space for advertising to the clients, wherein the software of the client device 102 can present the adds to the client.

Figure 3:
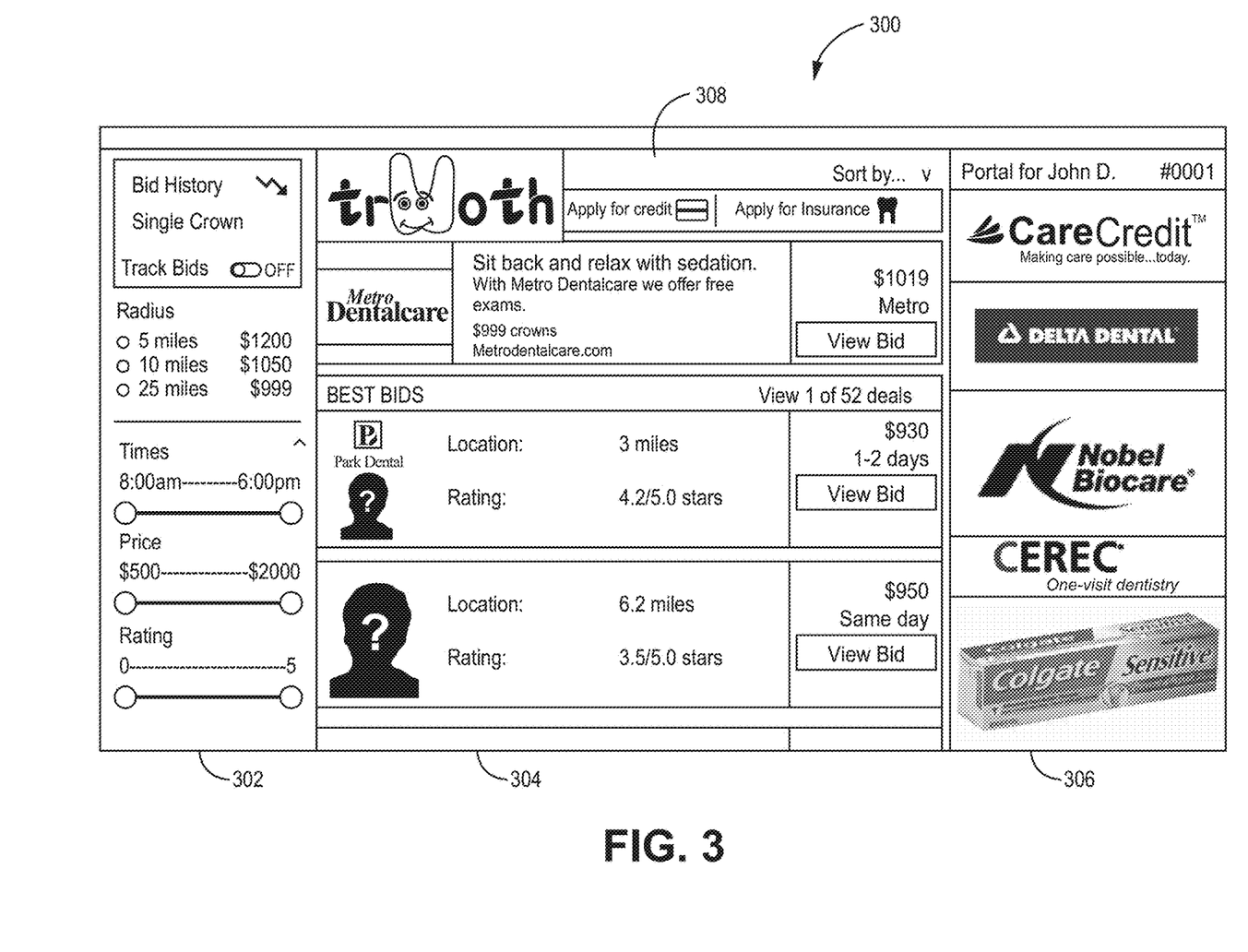
FIG. 3 is an illustration of an example page of an app or portal displayed by a client device in accordance with the method of FIG. 2.

FIG. 3 is an image of an example page 300 displayed by an app of a client device 104 that implements the client device portion of the method described above. The page 300 displays a left panel 302 with a plurality of filters to filter out bids for a service requested by the client device 104. The filters include a radius from the requested location, a time range for the service, a price range for the service, and a rating for the service provider. A summary of some of the bids are displayed in the center panel 304. Each summary includes a button to select to view details of the bid. A right panel 306 on the page 300 displays adds. A top panel 308 displays adds as well as buttons that allow the client to apply for credit or insurance through the system 100. In an example, the backend server 102 is communicatively coupled (e.g., over the Internet) with one or more devices from lending institutions willing to consider clients for credit. Selecting the "Apply for credit" button can connect the client to one or more of these institutions. In an example, the backend server 102 is communicatively coupled with one or more devices from insurance providers (e.g., over the Internet) willing to consider providing insurance to clients. Selecting the "Apply for Insurance" button can connect the client to the one or more insurance providers.

In an example, the backend server 102 can obfuscate the identity of the service provider when providing a bid and/or available service time to the client device 104 (block 214), and the client device 104 can display the bid to the client in a manner that obfuscates the identify of the service provider to the client. By obfuscating the identity of the service provider, the client does not know the identity prior to committing to a particular bid and/or service time. That is, the client device 104 can display obfuscated information regarding the identity of the service provider corresponding to the bid and/or available service time during selection/comparison of the bids/service times. By obfuscating the service provider identity, the client does not know who the specific service provider is when viewing an available service time or bid. The backend server 102 can provide the specific service provider identity for a bid and/or available service time after the backend server 102 has received in indication that the client has committed to (selected) a bid at block 222. Thus, the client is made aware of the specific service provider only after committing to a specific bid or available service time.

The backend server 102 can obfuscate the identity of the service provider by providing general information regarding the service provider without providing information that can specifically identify the service provider. In an example, the backend server 102 can obfuscate the service provider by identifying a general location for the service provider without providing their specific location. The general location can include a city limit, radius on map, zip code, or that the service provider is within the area of service identified by the client. Obfuscating the identity of the service provider can also include providing information to the client device 104 and/or displaying information to the client regarding the service provider without providing their street address, their business name, or any names of any individuals working at the service provider.

Figure 4:
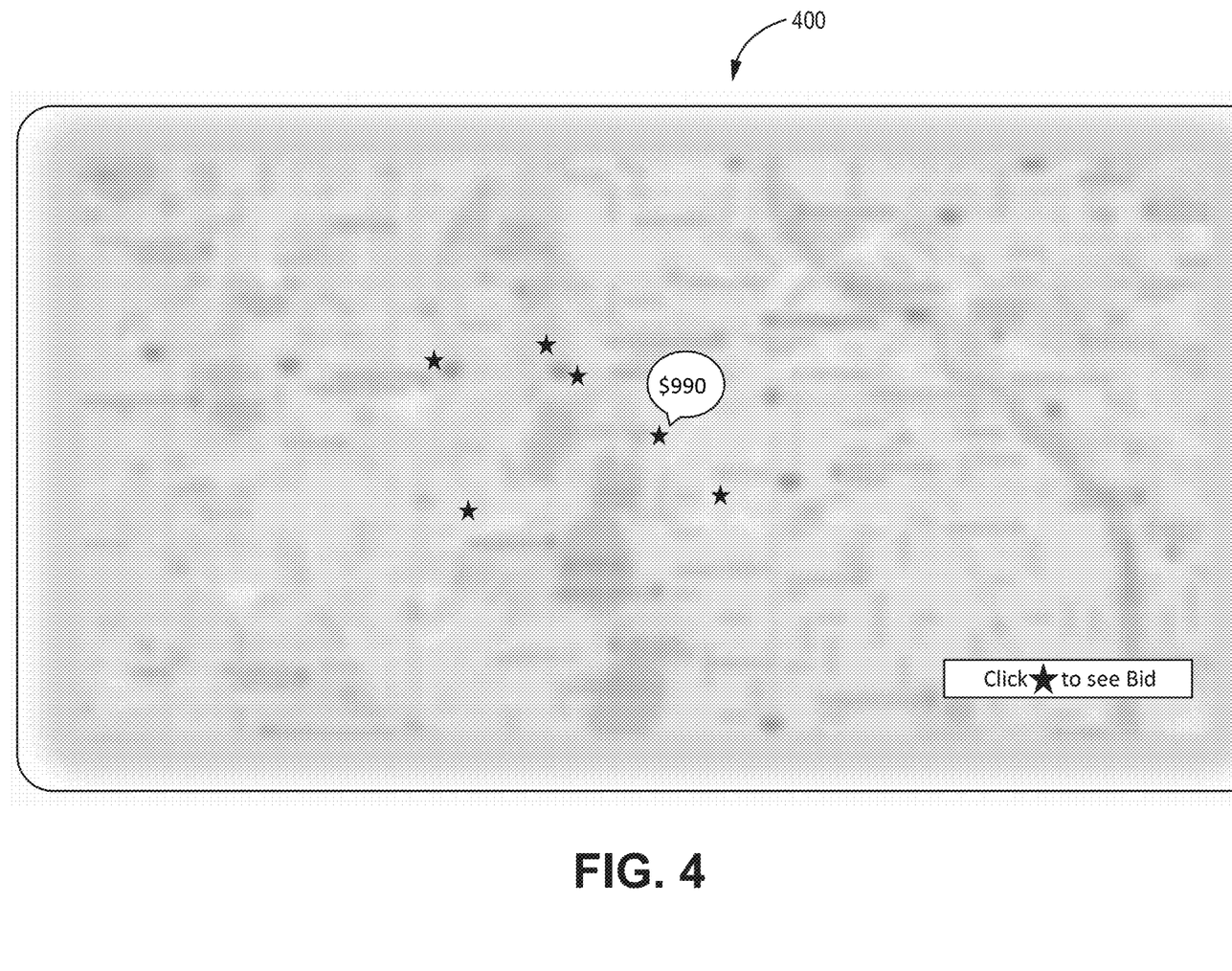
FIG. 4 is an illustration of an example manner of obfuscating the identity of a plurality of service provides in accordance with the method of FIG. 2.

FIG. 4 is an image of an example map 400 of bids displayed by the client device 104. The map 400 obfuscates the exact location in which the service will be performed by showing a blurry map. In this way, the client can visual a general location of each of the services without identifying the exact service provider. Other means can also be used to obfuscate the identity of the service provider, such as by showing a radiused area on the map within which the service provider is located.

Obfuscating the identity of the service can also include identifying the number of doctors, dentists, or other service providers in the office without naming any specific doctors, dentists, or other service providers. Obfuscating the identity of the service can also include identifying the type of office (e.g., general dentistry, dental surgery) without identifying the name of the office. Other means of obfuscating the identity can also be used.

Figure 5:
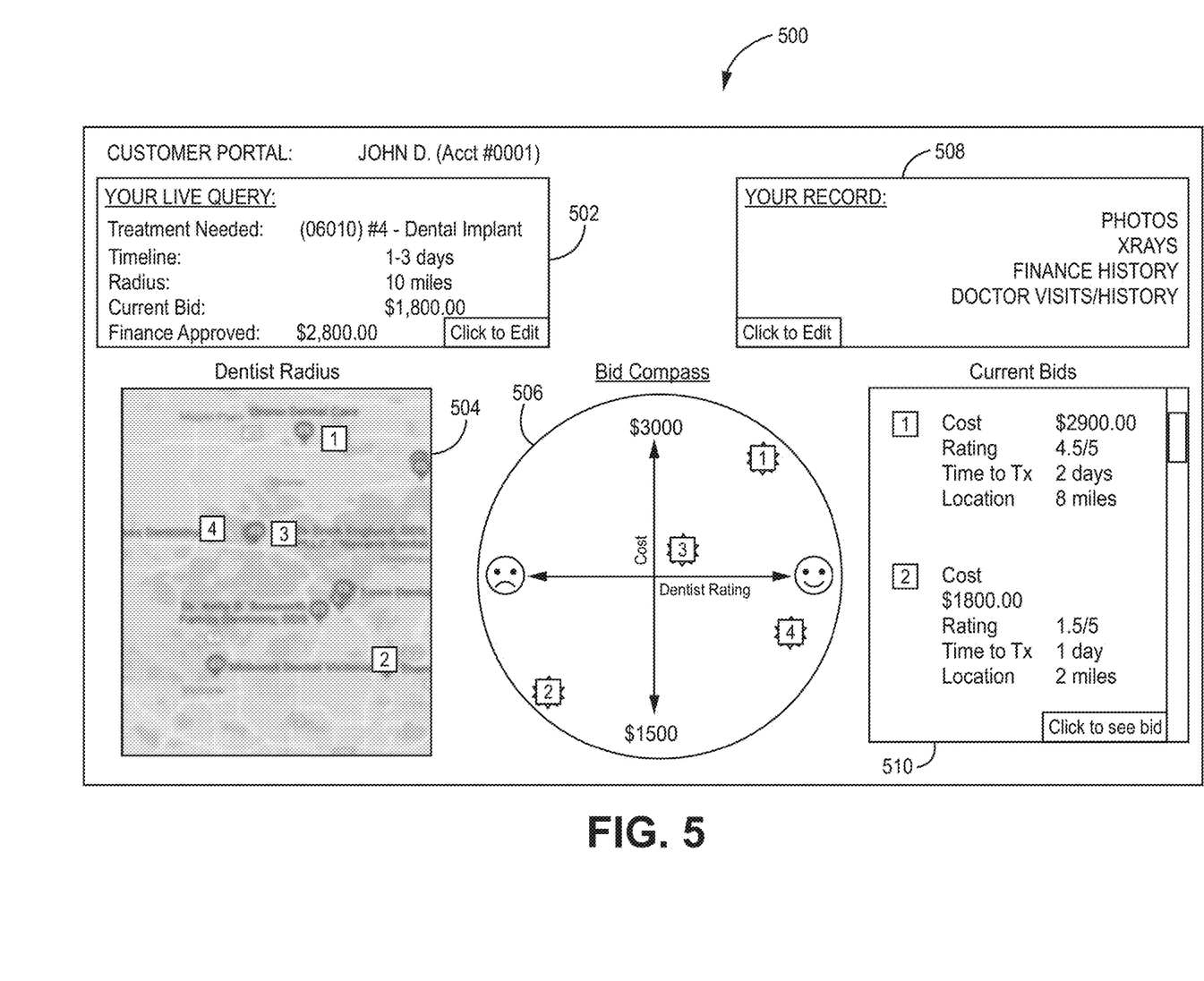
FIG. 5 is an illustration of another example page of an app or portal displayed by a client device in accordance with the method of FIG. 2.

FIG. 5 is another example image of a page 500 displayed by the app of the client device 104. The page 500 includes an upper left panel 502 illustrating the live request (query) in which the client is currently accepting bids. The lower left panel 504 illustrates a map of the location of different service providers that have submitted bids. The middle circle 506 is a graph illustrating the price of a bid for the requested service on one axis and rating for the service provider on the other axis. The upper right panel 508 illustrates links to other areas of the client account including photos, xrays, finance history, and doctor visits/history. The lower right panel 510 illustrates a summary of some of the bids received for the active request.

Figure 6:
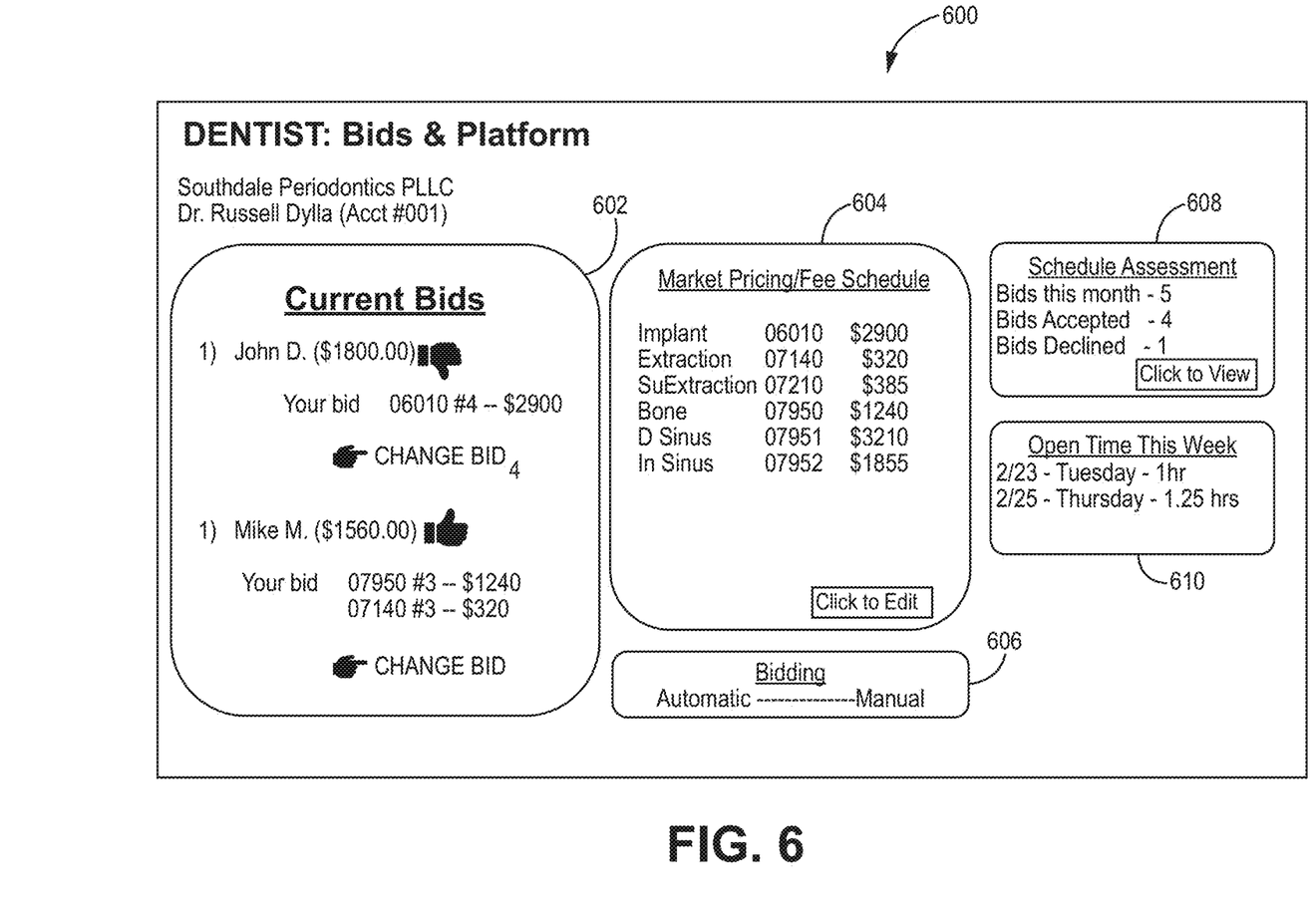
FIG. 6 is an illustration of a page/portal displayed by a service provider in accordance with the method of FIG. 2.

FIG. 6 is an image of a service provider portal 600 displayed by a provider device 106. The provider portal 600 includes a left panel 602 with a summary of currently active bids, a middle panel 604 listing items on the profile (e.g., fee schedule) for auto-bidding, a middle bottom panel 606 that allows the service provide to enable automatic bidding, an upper left panel 608 that shows a summary of the bids submitted by the service provider, and a lower left panel 610 that displays time available this week for service.

Figure 7:
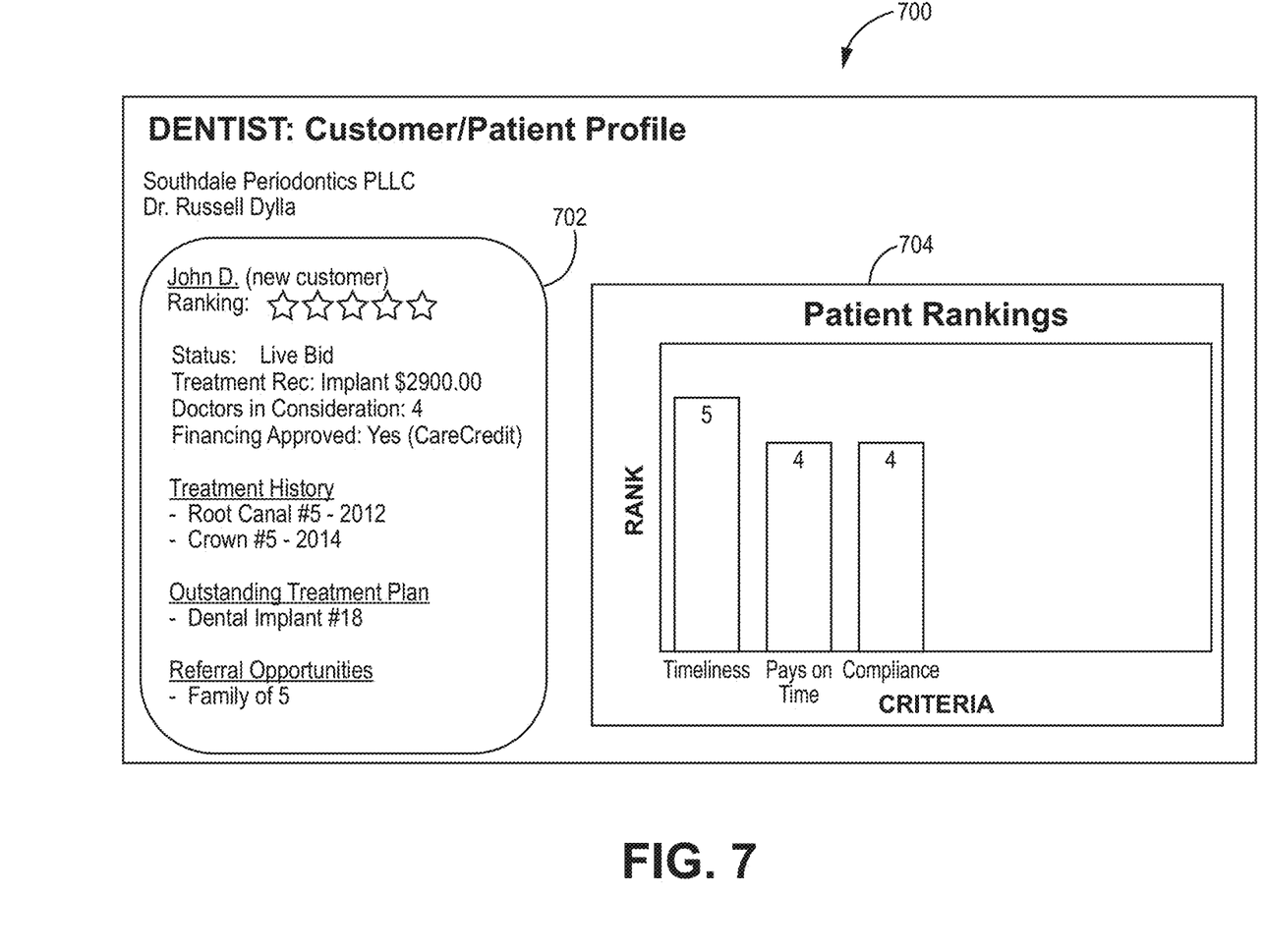
FIG. 7 is an illustration of another portion of the page/portal displayed by a service provider in accordance with the method of FIG. 2.

FIG. 7 is another image of a service provider portal 700 displayed by a provider device 106. The provider portal 700 illustrates a client information page displayed for the service provider. The client information page can provide information on the client for the service provider. In an example, the client information is obfuscated by, for example, only revealing the first name or first name and last name initial without other identifying information. The left panel 702 includes a ranking of the customer (e.g., based on a compilation of rankings from other service providers), information on any live bids out the client, the client's treatment history, outstanding treatment plan, and family. The right panel 704 illustrates metrics on the client such as their timeliness of showing up for service, timeliness of payment, and compliance.

As should be understood, multiple client devices 104 and multiple service provider devices 106 can be communicating with the backend server 102 contemporaneously to request, submit, and accept bids as well as perform the other actions described herein. Thus, the backend server 102 can concurrently process communications from multiple client devices 104 and provider devices 106.

Figure 8:
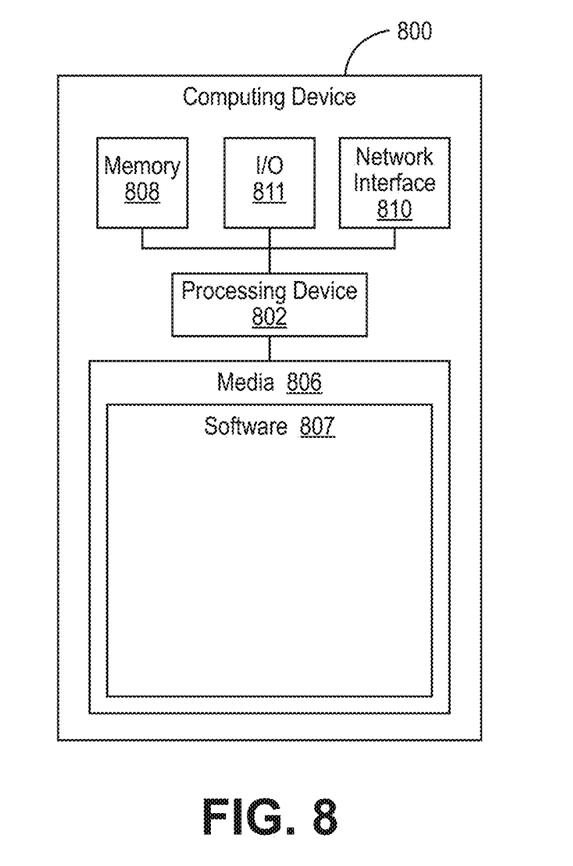
FIG. 8 is a block diagram of an example computing device, which can be a client device or a service provider device.

FIG. 8 is a block diagram of an example computing device 800, which can be a client device 104 or a provider device 106. Each client device 104 or provider device 106 executes software which causes the client device 104 or provider device 106 to implement the functionality described herein. This software can be a software module executing on a respective computing (e.g., mobile) device 800. Each respective computing device 800 includes one or more processing devices 802 for executing instructions 804. The one or more processing devices 802 can include a general-purpose processor or a special purpose processor. The instructions 804 are stored (or otherwise embodied) on or in an appropriate storage medium 806 or media (such a hard drive or other non-volatile storage) from which the instructions 804 are readable by the processing device(s) for execution thereby. The one or more processing devices 802 are coupled to the storage medium or media to access the instructions therefrom. The instructions 804 include the software 807 to implement the functions of the client device 104 or provider device 106.

The computing device 800 also includes memory 808 that is coupled to the processing device(s) 802 for storing instructions (and related data) during execution by the processing device(s) 802. Memory comprises, in one implementation, any suitable form of random-access memory (RAM) now known or later developed, such as dynamic random-access memory (DRAM). In other implementations, other types of memory are used. The computing device 800 also includes at least one network interface 810 (e.g., a wireless cellular interface, a wi-fi interface) for communicatively coupling to other computing devices over a network. The computing device 800 can also include one or more human interface devices (I/O) 811. The human interface can include any suitable interface that can provide information to and/or receive input from a human, including a touchscreen, a microphone, a speaker, a heads-up display, or a camera.

In an example, the instructions or a portion thereof can be stored or otherwise embodied on a computer readable medium that is distinct from any device and can be loaded onto a computing device 800. The computer readable media on which the instructions are stored can be any suitable computer readable media such as a magnetic media such as a hard disk drive (HDD), optical media such as a CD, DVD, Blu-Ray disk, or a non-volatile electric media such as a solid-state drive (SDD), flash media, or EEPROM. Such computer readable media can be standalone media (e.g., a USB stick or CD) or can be computer readable media within a computing device (e.g., a server or network accessible storage). The software 807 on the storage media 806 implementing the functionality for the client device 104 or provider device 106 can be an app or application that is installed on the computing device 800 or code from a web browser where the functionality is implemented in one or more web pages.

Figure 9:
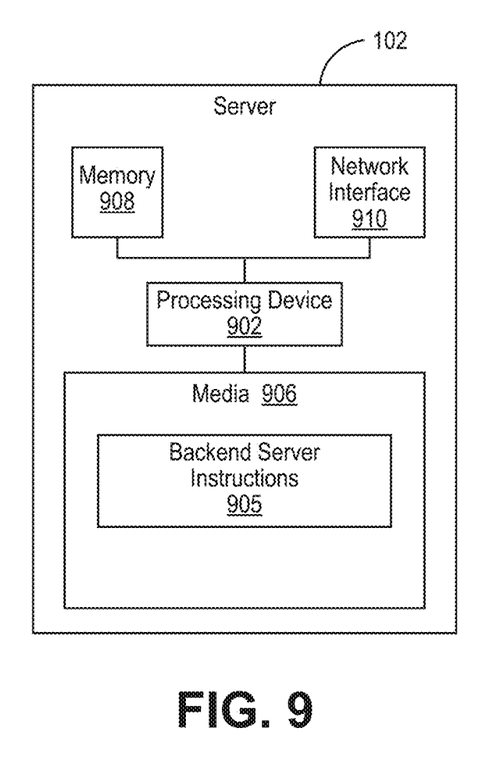
FIG. 9 is a block diagram of an example device for implementing the backend server in accordance with the method of FIG. 2.

FIG. 9 is a block diagram of an example backend server 102. The backend server 102 includes one or more processing devices 902 for executing instructions 904. The one or more processing devices 802 can include a general-purpose processor or a special purpose processor. The instructions 904 are stored (or otherwise embodied) on or in an appropriate storage medium 906 or media (such a hard drive or other non-volatile storage) from which the instructions 904 are readable by the processing device(s) for execution thereby. The one or more processing devices 902 are coupled to the storage medium or media to access the instructions therefrom. The instructions 904 include backend server instructions 905 which, when executed by the processing device(s) 902, cause the server 102 to perform the actions of the backend server 102 described herein.

The backend server 102 also includes memory 908 that is coupled to the processing device(s) 902 for storing instructions (and related data) during execution by the processing device(s) 902. Memory comprises, in one implementation, any suitable form of random-access memory (RAM) now known or later developed, such as dynamic random-access memory (DRAM). In other implementations, other types of memory are used. The backend server 102 also includes at least one network interface 9010 (e.g., a wireless cellular interface, a wi-fi interface) for communicatively coupling to other computing devices over a network.

In an example, the instructions or a portion thereof can be stored or otherwise embodied on a computer readable medium that is distinct from any device and can be loaded onto a backend server 102. The computer readable media on which the instructions are stored can be any suitable computer readable media such as a magnetic media such as a hard disk drive (HDD), optical media such as a CD, DVD, Blu-Ray disk, or a non-volatile electric media such as a solid-state drive (SDD), flash media, or EEPROM. Such computer readable media can be standalone media (e.g., a USB stick or CD) or can be computer readable media within a computing device (e.g., a server or network accessible storage).

Although a single device is shown in this example for the backend server 102, the backend server 102 can be implemented with multiple computing devices (e.g., multiple servers). The multiple computing devices can be co-located and/or one or more of the multiple computing devices can be disparately located.

What is claimed is:

1. A method for matching a client with a service provider, the method comprising:
    receiving a request for a service from a client device, the request including an indication of the service to be performed, an indication of one or more times to perform the service, and an indication of a location for the service;
    selecting one or more service providers based on the location indicated for the service;
    comparing the request to one or more profiles for the one or more service providers and to available services times for the one or more service providers;
    generating at least one bid for the service based on the one or more profiles, wherein generating at least one bid includes identifying a profile that indicates a price for the service indicated in the request and has at least one available service time that corresponds to a length of time for the service and matches the one or more times indicated in the request;
    sending the at least one bid to the client device, wherein sending the at least one bid includes obfuscating, to the client device, the identity of the one or more service providers corresponding to the at least one bid;
    receiving from the client device a selection of one of the at least one bids; and
    in response to the selection of a bid, sending to the client device, the specific identity of the one or more service providers.

2. The method of claim 1, wherein obfuscating the identity of the one or more service providers includes providing a general location for the one or more service providers without providing the specific location or name of the one or more service providers.

3. The method of claim 1, comprising:
    sending an indication of the request to at least one service provider for consideration of manual bids, wherein sending an indication of the request includes obfuscating the identity of the client to the at least one service provider;
    receiving one or more manual bids from the at least one service provider;
    sending the one or more manual bids to the client device; and
    receiving from the client device a selection of one of the at least one bids; and
    in response to the selection of a bid, sending to the service provider corresponding to the selected bid, the specific identity of the client.

4. The method of claim 3, wherein obfuscating the identity of the client includes sending an indication of an insurance plan for the client, and an indication of a credit rating for the client.

5. The method of claim 1, wherein the client is a dental patient and wherein the one or more service providers are one or more offices providing dental services.

6. A method for matching a client with a service provider, the method comprising:
    receiving a request for a service from a client device, the request including an indication of the service to be performed and an indication of a location for the service;
    selecting one or more service providers based on the location indicated for the service;
    comparing the request to one or more profiles for the one or more service providers and to available services times for the one or more service providers;
    generating a list of available service times for the request;
    sending the list of available service times to the client device, wherein sending the list includes obfuscating, to the client device, the identity of the one or more service providers corresponding each of the available service times in the list;
    receiving from the client device a selection of one of the available service times in the list of available service times; and
    in response to the selection of a service time, sending to the client device, the specific identity of the one or more service providers.

7. The method of claim 6, wherein obfuscating the identity of the one or more service providers includes providing a general location for the one or more service providers without providing the specific location or name of the one or more service providers.

8. A server comprising:
    one or more processing devices; and
    a processor readable medium coupled to the one or more processing devices, the processor readable medium having software stored thereon, the software, when executed by the one or more processing devices, configured to:
        receive a request for a service from a client device, the request including an indication of the service to be performed, an indication of one or more times to perform the service, and an indication of a location for the service;
        select one or more service providers based on the location indicated for the service;
        compare the request to one or more profiles for the one or more service providers and to available services times for the one or more service providers;
        generate at least one bid for the service based on the one or more profiles, wherein generating at least one bid includes identifying a profile that indicates a price for the service indicated in the request and has at least one available service time that corresponds to a length of time for the service and matches the one or more times indicated in the request;
        send the at least one bid to the client device, wherein send the at least one bid includes obfuscate, to the client device, the identity of the one or more service providers corresponding to the at least one bid;
        receive from the client device a selection of one of the at least one bids; and
        in response to the selection of a bid, send to the client device, the specific identity of the one or more service providers.

9. The server of claim 8, wherein obfuscate the identity of the one or more service providers includes provide a general location for the one or more service providers without providing the specific location or name of the one or more service providers.

10. The server of claim 9, comprising:
send an indication of the request to at least one service provider for consideration of manual bids, wherein sending an indication of the request includes obfuscate the identity of the client to the at least one service provider;
receive one or more manual bids from the at least one service provider;
send the one or more manual bids to the client device;
receive from the client device a selection of one of the at least one bids; and
in response to the selection of a bid, send to the service provider corresponding to the selected bid, the specific identity of the client.

11. The server of claim 10, wherein obfuscate the identity of the client includes send an indication of an insurance plan for the client, and an indication of a credit rating for the client.

12. The server of claim 8, wherein the client is a dental patient and wherein the one or more service providers are one or more offices providing dental services.

13. A server comprising:
one or more processing devices; and
a processor readable medium coupled to the one or more processing devices, the processor readable medium having software stored thereon, the software, when executed by the one or more processing devices, configured to:
receive a request for a service from a client device, the request including an indication of the service to be performed and an indication of a location for the service; selecting one or more service providers based on the location indicated for the service;
compare the request to one or more profiles for the one or more service providers and to available services times for the one or more service providers;
generate a list of available service times for the request;
send the list of available service times to the client device, wherein send the list includes obfuscate, to the client device, the identity of the one or more service providers corresponding each of the available service times in the list;
receive from the client device a selection of one of the available service times in the list of available service times; and
in response to the selection of a service time, send to the client device, the specific identity of the one or more service providers.

14. The server of claim 13, wherein obfuscate the identity of the one or more service providers includes provide a general location for the one or more service providers without providing the specific location or name of the one or more service providers.

* * * * *